United States Patent
Kim

(10) Patent No.: US 12,235,382 B2
(45) Date of Patent: Feb. 25, 2025

(54) METHOD FOR REMOVING RANDOM NOISE OF RADAR COLLECTION SIGNAL IN BIOMETRIC SIGNAL MEASUREMENT RADAR, AND APPARATUS FOR SAME

(71) Applicant: JCFTECHNOLOGY CO., LTD., Seoul (KR)

(72) Inventor: Jin Myung Kim, Bucheon-si (KR)

(73) Assignee: JCTECHNOLOGY CO., LTD., Seoul (KR)

( * ) Notice: Subject to any disclaimer, the term of this patent is extended or adjusted under 35 U.S.C. 154(b) by 493 days.

(21) Appl. No.: 17/775,512

(22) PCT Filed: Nov. 11, 2019

(86) PCT No.: PCT/KR2019/015255
§ 371 (c)(1),
(2) Date: May 9, 2022

(87) PCT Pub. No.: WO2021/095893
PCT Pub. Date: May 20, 2021

(65) Prior Publication Data
US 2022/0381877 A1   Dec. 1, 2022

(30) Foreign Application Priority Data

Nov. 11, 2019  (KR) .................. 10-2019-0143162

(51) Int. Cl.
*G01S 7/295* (2006.01)
*G01S 7/292* (2006.01)
*G01S 7/41* (2006.01)

(52) U.S. Cl.
CPC ............ *G01S 7/2922* (2013.01); *G01S 7/295* (2013.01); *G01S 7/415* (2013.01)

(58) Field of Classification Search
CPC ..... A61B 5/024; A61B 5/0507; A61B 5/0816; A61B 5/7203; A61B 5/7257;
(Continued)

(56) References Cited

U.S. PATENT DOCUMENTS

| | | | |
|---|---|---|---|
| 2008/0074307 | A1 | 3/2008 | Boric-Lubecke et al. |
| 2008/0077015 | A1 | 3/2008 | Boric-Lubecke et al. |
| 2016/0336989 | A1 | 11/2016 | Lin et al. |

FOREIGN PATENT DOCUMENTS

| | | |
|---|---|---|
| CN | 111812629 A | 10/2020 |
| JP | 2009-501044 A | 1/2009 |

(Continued)

OTHER PUBLICATIONS

International Search Report issued on Aug. 7, 2020, in connection with International Patent Application No. PCT/KR2019/015255, along with an English translation.
(Continued)

*Primary Examiner* — Timothy A Brainard
(74) *Attorney, Agent, or Firm* — NKL LAW; Jae Youn Kim

(57) ABSTRACT

The present invention relates to a method of effectively removing various vibration noises using microwave Doppler radar, and an apparatus therefor. The method comprises the steps of: (a) generating and transmitting an oscillation frequency to a dynamic target, and receiving a signal
(Continued)

reflected from the dynamic target and various signals generated around the dynamic target; (b) generating a Doppler IF signal from each of n received signals; (c) converting each Doppler IF signal into digital data; (d) configuring digital signals into a data set, and converting the data set into a frequency component symbol set; (e) calculating a value by adding index symbols and dividing by n reception antennas; and (f) classifying deviation between spectrum components of a commonly-generated periodic signal and an uncommon aperiodic signal, and obtaining only a periodic signal through filtering. The present invention can improve accuracy of sensing a biometric signal.

4 Claims, 7 Drawing Sheets

(58) Field of Classification Search
CPC ....... A61B 5/7225; A61B 5/725; G01S 13/56; G01S 7/2883; G01S 7/2922; G01S 7/2923; G01S 7/295; G01S 7/415; Y02A 90/10
See application file for complete search history.

(56) References Cited

FOREIGN PATENT DOCUMENTS

| | | | |
|---|---|---|---|
| JP | 2012-130391 | A | 7/2012 |
| JP | 2012-235891 | A | 12/2012 |
| JP | 2016-057168 | A | 4/2016 |
| JP | 2016-156754 | A | 9/2016 |
| JP | 2016-168177 | A | 9/2016 |
| JP | 2016-174869 | A | 10/2016 |
| JP | 2017-129558 | A | 7/2017 |
| JP | 2017-225834 | A | 12/2017 |
| KR | 10-2011-0008080 | A | 1/2011 |
| KR | 10-2018-0010713 | A | 1/2018 |
| KR | 10-2018-0037528 | A | 4/2018 |
| KR | 10-1948386 | B1 | 2/2019 |
| WO | WO-2010046661 | A1 * | 4/2010 ......... H01S 3/06758 |

OTHER PUBLICATIONS

Written Opinion issued on Aug. 7, 2020, in connection with International Patent Application No. PCT/KR2019/015255.

* cited by examiner

FIG. 6

| Antenna \ Index | I(1) | I(2) | I(3) | ... | I(m) |
|---|---|---|---|---|---|
| Rx(1) | a1 | a2 | a3 | ... | a(m) |
| Rx(2) | b1 | b2 | b3 | ... | b(m) |
| Rx(3) | c1 | c2 | c3 | ... | c(m) |
| ⋮ | ⋮ | ⋮ | ⋮ | ⋮ | ⋮ |
| Rx(n) | (n)1 | (n)2 | (n)3 | ... | (n)(m) |

METHOD FOR REMOVING RANDOM NOISE OF RADAR COLLECTION SIGNAL IN BIOMETRIC SIGNAL MEASUREMENT RADAR, AND APPARATUS FOR SAME

CROSS-REFERENCE TO RELATED APPLICATION

The present application is a national stage filing under 35 U.S.C § 371 of PCT application number PCT/KR2019/015255 filed on Nov. 11, 2019 which is based upon and claims the benefit of priorities to Korean Patent Application Nos. 10-2019-0143162 filed on Nov. 11, 2019 in the Korean Intellectual Property Office. The disclosures of the above-listed applications are hereby incorporated by reference herein in their entireties.

TECHNICAL FIELD

The present invention relates to a method for effectively reducing and removing, by using microwave Doppler radar, various types of vibration noise introduced from the outside while biometric signals of a human body are acquired, and an apparatus for same.

BACKGROUND ART

Generally, as one of sensing techniques, radar may accurately measure an exact distance to an object and a relative speed of the object with respect to an observation point. Radar devices usually operate by emitting electromagnetic waves of microwave level to an object and receiving the electromagnetic waves reflected from the object. A processed signal is converted into a form that can be used by an operator or peripherals controlled by the radar. A technique of detecting movement or biometric signals using radar is commercialized. Methods for solving various noise problems included in a radar reception signal caused by external influences that may occur in an environment in which the radar is actually used are proposed.

In addition, Doppler radar uses the Doppler effect of radio waves to detect a moving target on the basis of the difference between the frequency of radar waves transmitted toward a target object and the frequency of reflected radio waves. It is used for weather radar, self-contained navigation systems of aircrafts, and military radar. For meteorological purpose, a change in the speed of wind generated inside a cloud is measured. The self-contained navigation system calculates a current position by measuring the speed of radio waves reaching the ground. Pulse Doppler radar, which generally uses a single pulse signal to capture and track only a target moving in the reflected waves on the surfaces of the ground and the sea, is the mainstream of military radar.

In FIG. 1, in a method of measuring biometric signals using conventional microwave radar, it is common to sense the biometric signals by collecting Doppler effects generated according to vibration or movement of a human body generated by heartbeat, respiration or the like as data.

However, in the process of measuring biometric signals of an actual human body, additional Doppler effects occur due to movement of the human body, movement of muscles, or surrounding environmental factors. Accordingly, in FIG. 2, in the collection signal actually sensed by the radar, random noises are loaded together in the same temporal and frequency region where the biometric signals exist, in addition to the biometric signal data. The random noises lack periodicity and thus have a characteristic of appearing while variously changing over time, whereas the biometric signal has a characteristic of maintaining a predetermined periodic pattern. Therefore, researches that can distinguish biometric signals from noises by calculating the difference with the random noises mixed in the human heartbeat spectrum region should be conducted.

As a prior art related to the present invention, Patent Document 1 discloses a method of determining biometric information of a target, the method comprising the steps of: generating a frame set by accumulating single frames overlapped with a radar pulse reflected from a target for measuring heartbeat according to a reception time set in advance; removing a single frame in which a transition period of a maximum peak is generated by movement of the target, by using a first sampler index indicating the maximum peak for each of the single frames included in the generated frame set and a second sampler index that is a sampler index corresponding to the most frequent maximum peak among the first sampler indices; and determining a heartbeat frequency of the target by applying an algorithm of identifying a peak frequency by detecting a periodic pattern of incomplete data for a frame set including a period that is emptied as a single frame in which the transition period of the maximum peak is generated by the movement of the target is removed, wherein the radar pulse reflected from the target is a radar signal that reflects movement of the target, and the step of removing a portion in which the transition period is generated includes the steps of: extracting a first sampler index indicating a maximum peak for each of the single frames included in the frame set; determining a sampler index corresponding to the largest number of maximum peaks among the first sampler indices indicating the maximum peak as a second sampler index indicating a criterion for generating a motion profile; generating the motion profile based on the movement of the target by using a difference between the first sampler index and the second sampler index; and aligning the single frames included in the frame set using the motion profile.

In addition, Patent Document 2 discloses a multi-carrier Doppler radar that measures Doppler, after transmitting a baseband signal, based on a baseband signal reflected from an object. The multi-carrier Doppler radar includes a signal processing part which uses a baseband signal including multi-carriers as the baseband signal, converts the received baseband signal into N frequency signals through Fourier transform, selects any M frequency signals out of the N converted frequencies, multiplies the selected M frequency signals by a calibration constant to extract the phase values of the M frequency signals to be outputted, and outputs a Doppler measurement value by applying a filter to each of M distance information outputted by multiplying each of extracted M phase values by a distance conversion constant and summing the output values.

PRIOR ART DOCUMENT

Patent Documents (Patent Document 1) Korean Patent Publication No. 10-1948386 (published on Feb. 14, 2019)
(Patent Document 2) Korean Patent Publication No. 10-2018-0010713 (published on Jan. 31, 2018)

DISCLOSURE OF INVENTION

Technical Problem

An object of the present invention is to effectively remove random noises when the random noises are mixed in a biometric signal area that has periodicity comparatively.

Another object of the present invention is to improve accuracy of measuring biometric signals in a contactless manner using microwave radar.

Technical Solution

To accomplish the above object, according to one aspect of the present invention, there is provided a method of removing random noises of a radar collection signal in a biometric signal measurement radar, the method comprising the steps of: (a) generating, by a voltage-controlled oscillator (VCO) of an IF signal generator, an oscillation frequency of a predetermined period using a voltage V(t) applied from the outside, transmitting the generated oscillation frequency to a major portion of a dynamic target through a single transmission antenna, and receiving, by n reception antennas, a signal reflected from the dynamic target and various types of signals generated around the dynamic target; (b) generating, by the IF signal generator, a Doppler IF signal from each of the n received signals; (c) converting, by an analog/digital converter, each of multiple Doppler IF signals input from the IF signal generator into digital data; (d) configuring digital signals collected by the analog/digital converter during a unit time into a data set having symbols at sampling time intervals by a Fast Fourier Transformer, and converting the data set into a frequency component symbol set having multiple indices; (e) calculating a value by adding, for each index set, index symbols converted into a frequency component symbol set and then dividing by the number of the n reception antennas by a calculation unit of a signal calculator; and (f) classifying deviation between spectrum components of a commonly-generated periodic signal and an uncommon aperiodic signal, for the value calculated by the calculation unit, according to a predetermined reference threshold value, and obtaining only the periodic signal through filtering.

In addition, in the present invention, there is provided an apparatus for removing random noises of a radar collection signal in a biometric signal measurement radar, the apparatus comprising: an IF signal generator for generating an oscillation frequency of a predetermined period using a voltage V(t) applied from the outside by a voltage-controlled oscillator and transmitting the oscillation frequency through a single transmission antenna Tx, receiving a reflection wave reflected from a radar signal collection area including a dynamic target at a predetermined distance through a plurality of reception antennas Rx-1 to Rx-n, and generating a Doppler IF signal from the received n signals; an analog/digital converter for converting the n analog signals generated by the IF signal generator into digital signals; a signal calculator for configuring the digital signals collected by the analog/digital converter during a unit time into a data set having symbols at sampling time intervals by a Fast Fourier Transformer, converting the configured data set into a frequency component symbol set of indices, and calculating a value by adding, for each index set, index symbols and then dividing by the number of the n reception antennas Rx by the calculation unit; and a digital filtering signal processor for filtering after classifying deviation between spectrum components of a commonly-generated periodic signal and an uncommon aperiodic signal, for the value calculated by the signal calculator, according to a predetermined reference threshold value.

In addition, in the present invention, the reception antennas Rx-1 to Rx-n may be arranged in a position and direction capable of simultaneously receiving signals from the dynamic target and other areas.

In addition, in the present invention, in the digital filtering signal processor, any one among a band-pass filter (BPF), a high-pass filter (HPF), or a low-pass filter (LPF) of a predetermined band may be applied in order to filter according to a reference threshold value.

Advantageous Effects

According to the present invention, there is an advantage of improving accuracy of sensing biometric signals by effectively reducing and removing random noises when the random noises contained in a biometric signal area are mixed in the biometric signal area having periodicity comparatively, by using a contactless biometric signal measurement Doppler radar including a single transmitter and a plurality of receivers.

BRIEF DESCRIPTION OF THE DRAWINGS

FIG. 6 is a table showing a frequency component symbol set of a plurality of indices through Fourier transform for removing random noises of a radar collection signal in a biometric signal measurement radar according to the present invention.

BEST MODE FOR CARRYING OUT THE INVENTION

Hereinafter, an embodiment of an apparatus for removing random noises of a radar collection signal in a biometric signal measurement radar according to the present invention will be described in detail with reference to the accompanying drawings.

Figure 1:
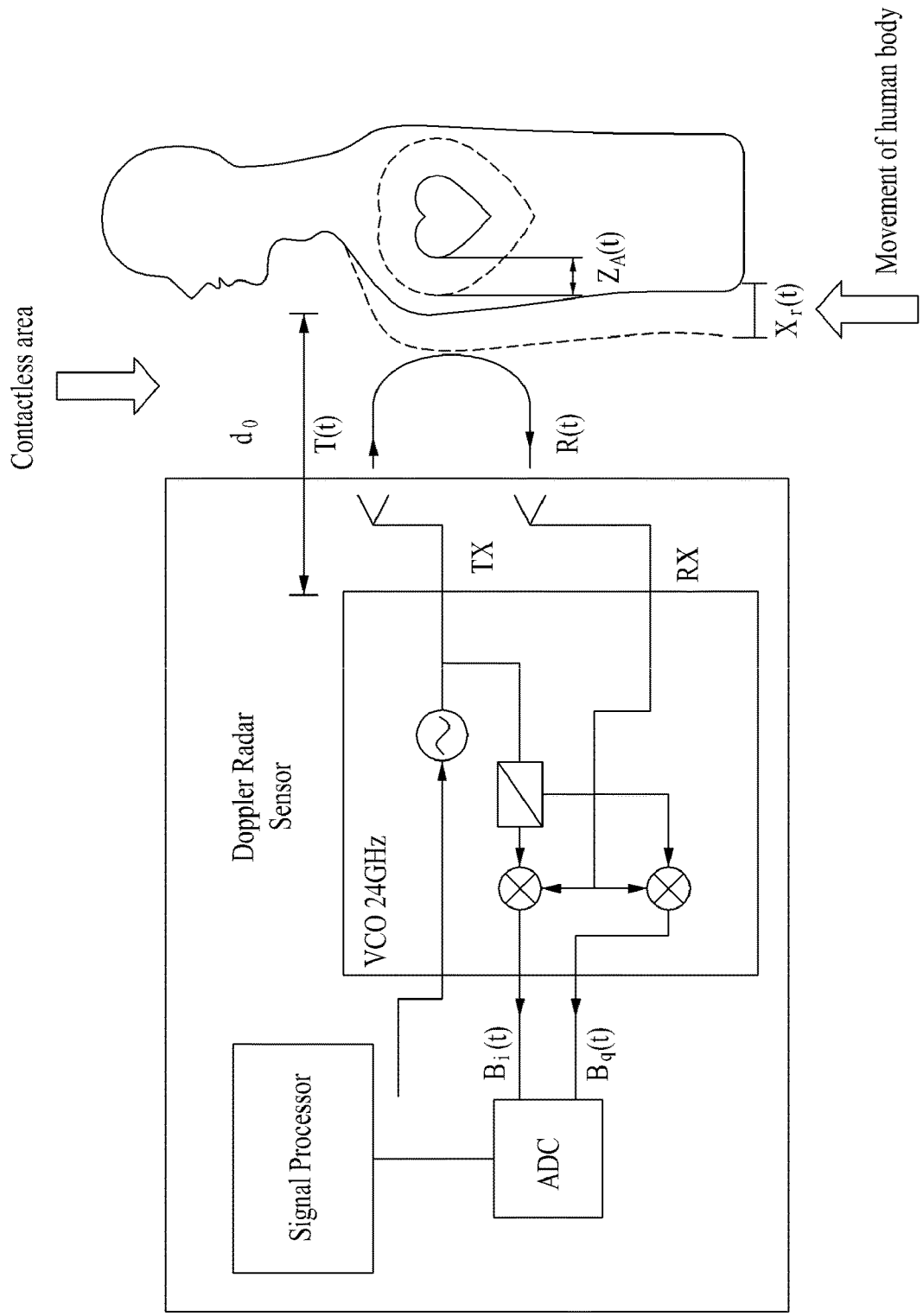
FIG. 1 is a block diagram showing the concept of a general biometric signal measurement radar.
Figure 2:
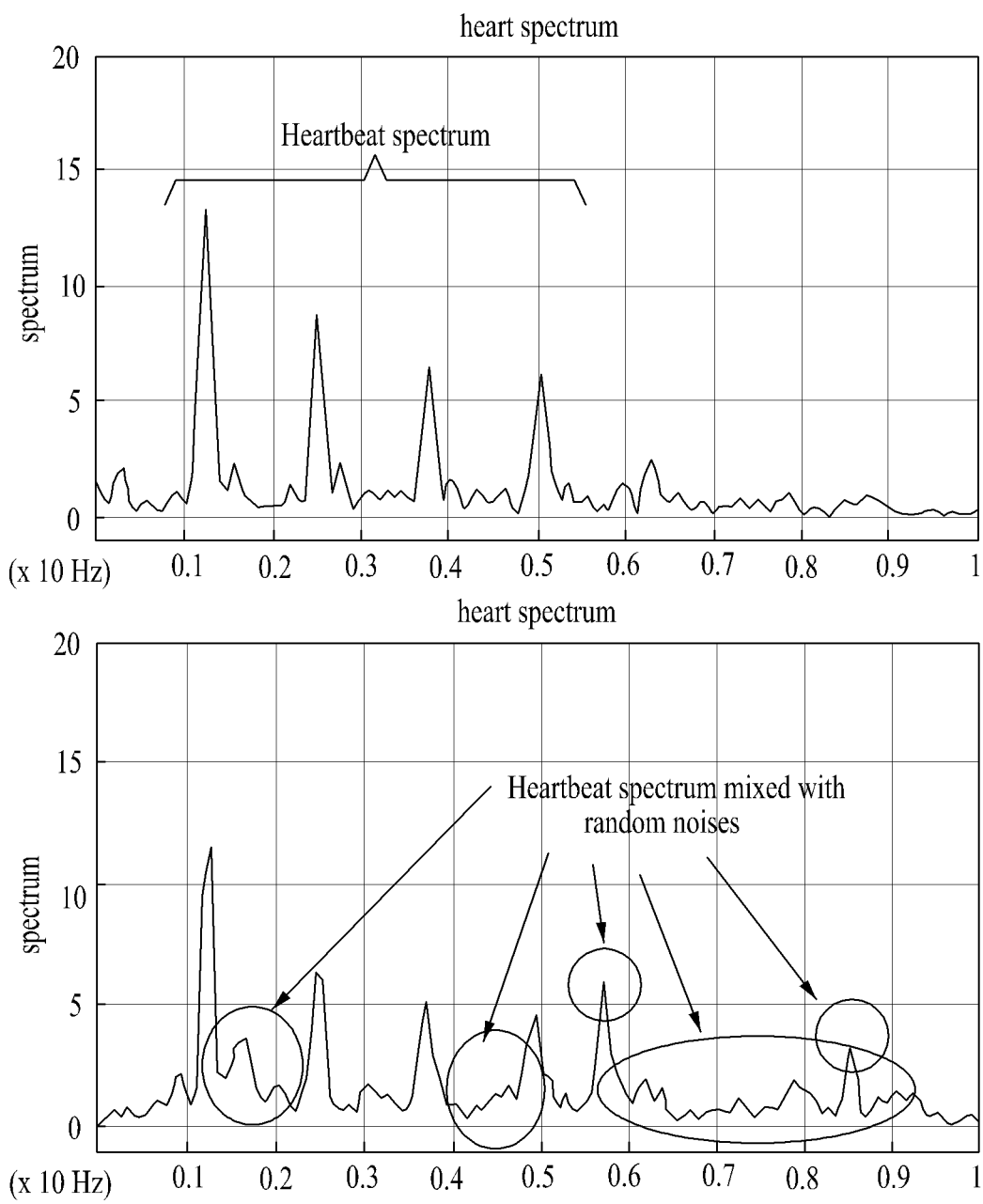
FIG. 2 is a view of graphs showing a heartbeat spectrum and a heartbeat spectrum mixed with random noises as a biometric signal, respectively.
Figure 3:
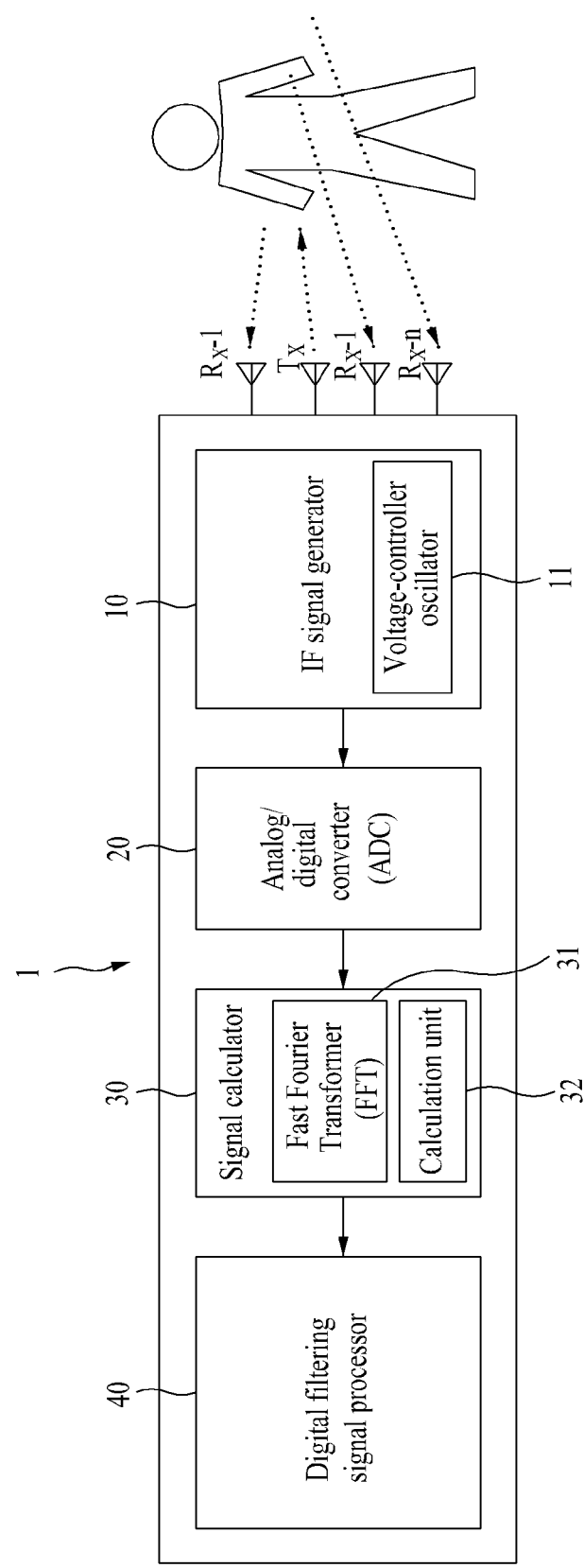
FIG. 3 is a block diagram showing an apparatus for removing random noises of a radar collection signal in a biometric signal measurement radar according to an embodiment of the present invention.
Figure 4:
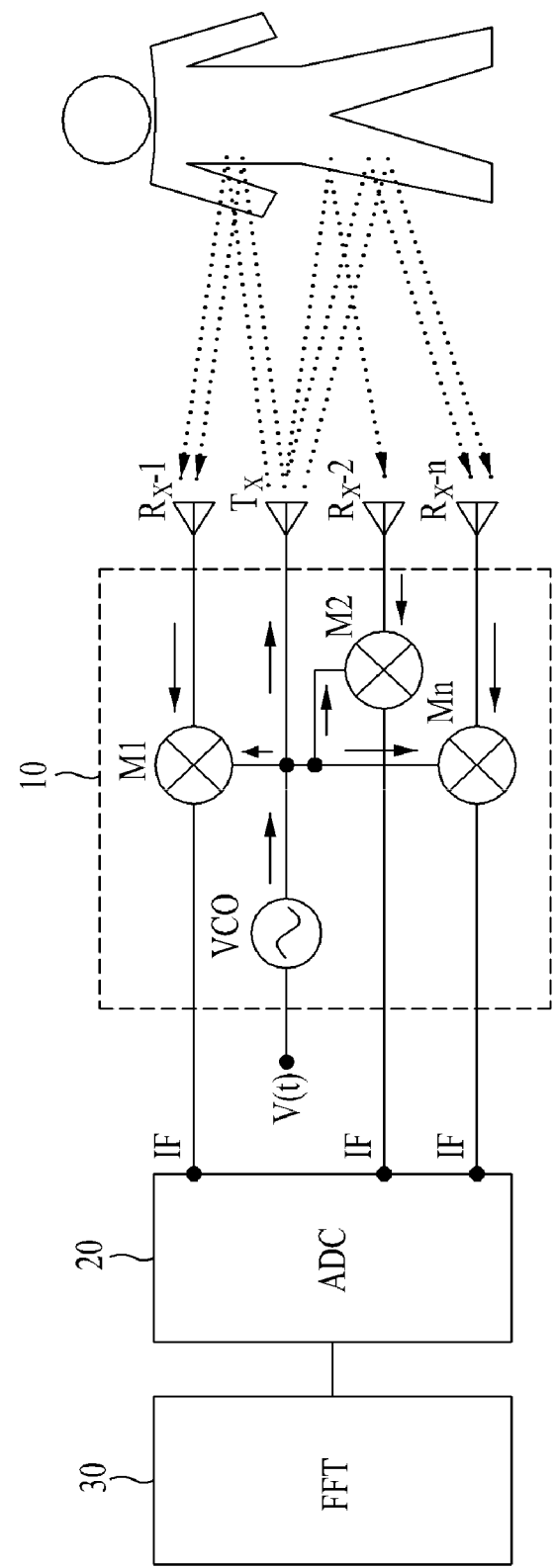
FIG. 4 is a view showing the configuration of an apparatus for removing random noises of a radar collection signal in a biometric signal measurement radar according to the present invention.

In FIGS. 3 and 4, an Intermediate Frequency (IF) signal generator 10 of a microwave Doppler radar 1 generates an IF signal from a difference between an oscillation frequency generated by a voltage-controlled oscillator (VCO) 11 and a received frequency. The IF signal generator 10 includes a transmission antenna that transmits an oscillation frequency of a predetermined period output from the voltage-controlled oscillator 11 to the outside. In addition, the IF signal generator 10 includes a reception antenna for receiving a signal transmitted from the transmission antenna and reflected by a dynamic target, for example, a human body, located at a certain distance, and a signal transmitted from a radar signal collection area around the human body. Here, the transmission antenna Tx is configured as a single antenna, and the reception antennas Rx-1 to Rx-n are configured in plurality. It is preferable that the reception antennas Rx-1 to Rx-n are arranged in an appropriate position and direction to simultaneously receive signals from the dynamic target and other areas.

In addition, in the IF signal generator 10, mixers M1 to Mn are coupled to the reception antennas Rx-1 to Rx-n, respectively. The mixers M1 to Mn generate Doppler IF signals on the basis of the difference between the oscillation frequency output from the voltage-controlled oscillator 11 and n signals received through the reception antennas Rx-1 to Rx-n.

The IF signal generator 10 has a structure the same as that of a Doppler radar transceiver capable of transmitting and receiving signals, and includes a single transmission antenna Tx and a plurality of reception antennas Rx-1 to Rx-n. Therefore, in the IF signal generator 10, the voltage-controlled oscillator 11 generates an oscillation frequency of a predetermined period using a voltage V(t) applied from the outside, transmits the oscillation frequency through the single transmission antenna Tx, receives a reflection wave reflected from a radar signal collection area including a dynamic target at a predetermined distance through the plurality of reception antennas Rx-1 to Rx-n, and generates Doppler IF signals from the received n signals.

The analog/digital converter 20 converts and outputs an input analog signal as a digital signal, and it converts n analog signals generated by the IF signal generator 10 into a digital signal and outputs the digital signal. At this point, since Fast Fourier Transform should be performed to convert the digital signal into a frequency symbol, a data set is formed at sampling time intervals using data of digital signals collected during a unit time.

The signal calculator 30 includes a Fast Fourier Transformer (FFT) and a calculation unit 32. The Fast Fourier Transformer 31 converts the data set of the digital signals collected during a unit time by the analog/digital converter 20 into symbols of frequency components, and this is configured of n spectrum index data sets. Then, the calculation unit 32 obtains a value by adding the configured spectrum index symbols for each index set and dividing by the number of the n reception antennas Rx-1 to Rx-n.

The digital filtering signal processor 40 performs filtering after classifying deviation between spectrum components of a commonly-generated periodic signal and an uncommon aperiodic signal, for the value obtained by the signal calculator 30 during a unit time, according to a predetermined reference threshold value. That is, although the result of the operation on a signal having periodicity, which is commonly generated during a unit time, is maintained as a value of a predetermined magnitude, since a signal having uncommon aperiodicity is lowered to a remarkably small value, the digital filtering signal processor 40 makes the deviation between the spectrum components of the periodic signal and the aperiodic signal large, and then processes the signals by classifying and filtering according to an appropriate reference threshold value. As the filter for filtering according to a reference threshold value, a band pass filter (BPF), a high pass filter (HPF), or a low pass filter (LPF) of a predetermined band may be appropriately selected.

A method of removing random noises of a radar collection signal in a biometric signal measurement radar according to the present invention configured as described above will be described.

Figure 5:
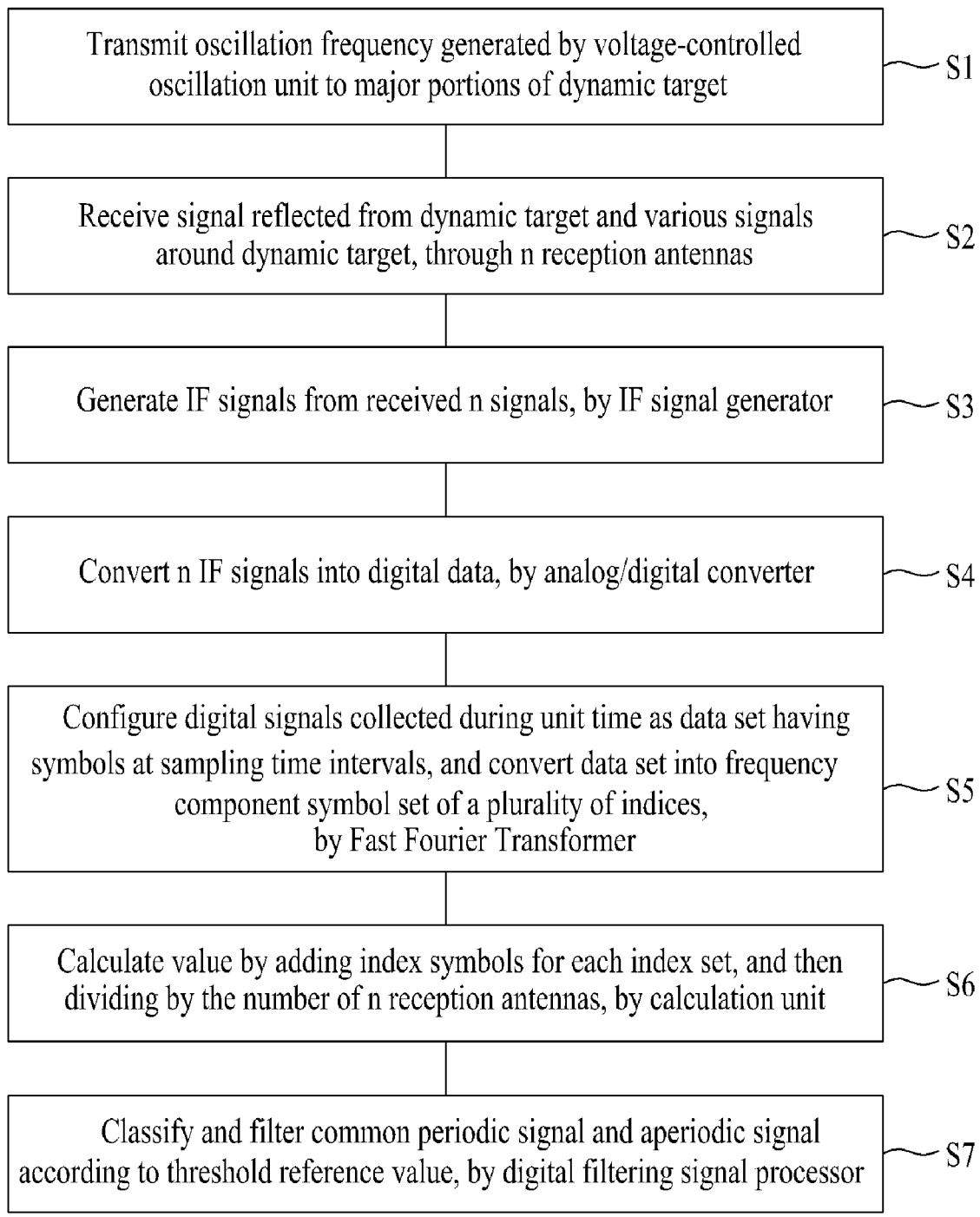
FIG. 5 is a flowchart illustrating a method of removing random noises of a radar collection signal in a biometric signal measurement radar according to the present invention.

First, in FIG. 5, the voltage-controlled oscillation unit 11 of the IF signal generator 10 generates an oscillation frequency of a predetermined period using a voltage V(t) applied from the outside, and transmits the oscillation frequency to major portions of a dynamic target through the transmission antenna Tx (S1). In addition, it is preferable to transmit the signal transmitted from the transmission antenna Tx, toward a portion of a human body that may best collect biological signals, which is the dynamic target.

The signal reflected from the dynamic target and various signals around the dynamic target are received through n reception antennas Rx-1 to Rx-n (S2). At this point, the n reception antennas Rx-1 to Rx-n include a reception antenna Rx-1 that receives signals containing the largest number of biometric signals, and a plurality of reception antennas Rx-2 to Rx-n that receive signals containing other movements of the human body, sound effects generated in the vicinity, or the like, in addition to the biometric signals.

The IF signal generator 10 generates Doppler IF signals from the n signals received through the plurality of reception antennas Rx-1 to Rx-n (S3). In addition, the analog/digital converter 20 converts a plurality of Doppler IF signals input after being generated by the IF signal generator 10 into digital data (S4). Since the digital data is continuously repeated over time while the plurality of reception antennas Rx-1 to Rx-n receives signals, data may be continuously collected by unit time in real-time.

The fast Fourier Transformer 31 of the signal calculator 30 generates a data set having symbols at sampling time intervals from the digital signal collected during a unit time by the analog/digital converter 20, and this data set is converted into a frequency component symbol set of a plurality of indices (S5).

Meanwhile, spectrum transform of the Doppler IF signal is performed in the following process. That is, in the spectrum transform of a frequency component, a signal in time domain collected during a predetermined period of time is transformed into a frequency component by finding periodicity. Therefore, digital sampling data of time domain collected during a predetermined period of time is required for Fast Fourier Transform. In addition, the symbol of the sampling time interval is the symbol of an original signal component sampled as a digital signal in the time domain. For example, when the time domain signal data for 30 seconds is collected and Fourier transform is performed thereon, spectrums of the frequency components of all signals showing periodicity is expressed for 30 seconds. At this point, the horizontal axis on the spectrum graph becomes the frequency axis, and this is the spectrum index.

In the table of FIG. 6, a plurality of indices is converted into frequency component symbol sets of I(m) while passing through the Fast Fourier Transformer 31. In addition, the calculation unit 32 calculates a value by adding the index symbols respectively acquired from the plurality of reception antennas Rx-1 to Rx-n for each index set I(1), I(2), I(3), . . . I(m), and dividing by the number of the n reception antennas Rx-1 to Rx-n (S6).

Here, signals of the n reception antennas Rx-1 to Rx-n are expressed as n spectrum index data, and the operation is performed by index set, which is the same spectrum component of each antenna. In addition, those expressed as I(2), I(3), . . . I(m) are actual frequency (Hz) components, and this symbol data represents spectrum intensity.

Figure 7:
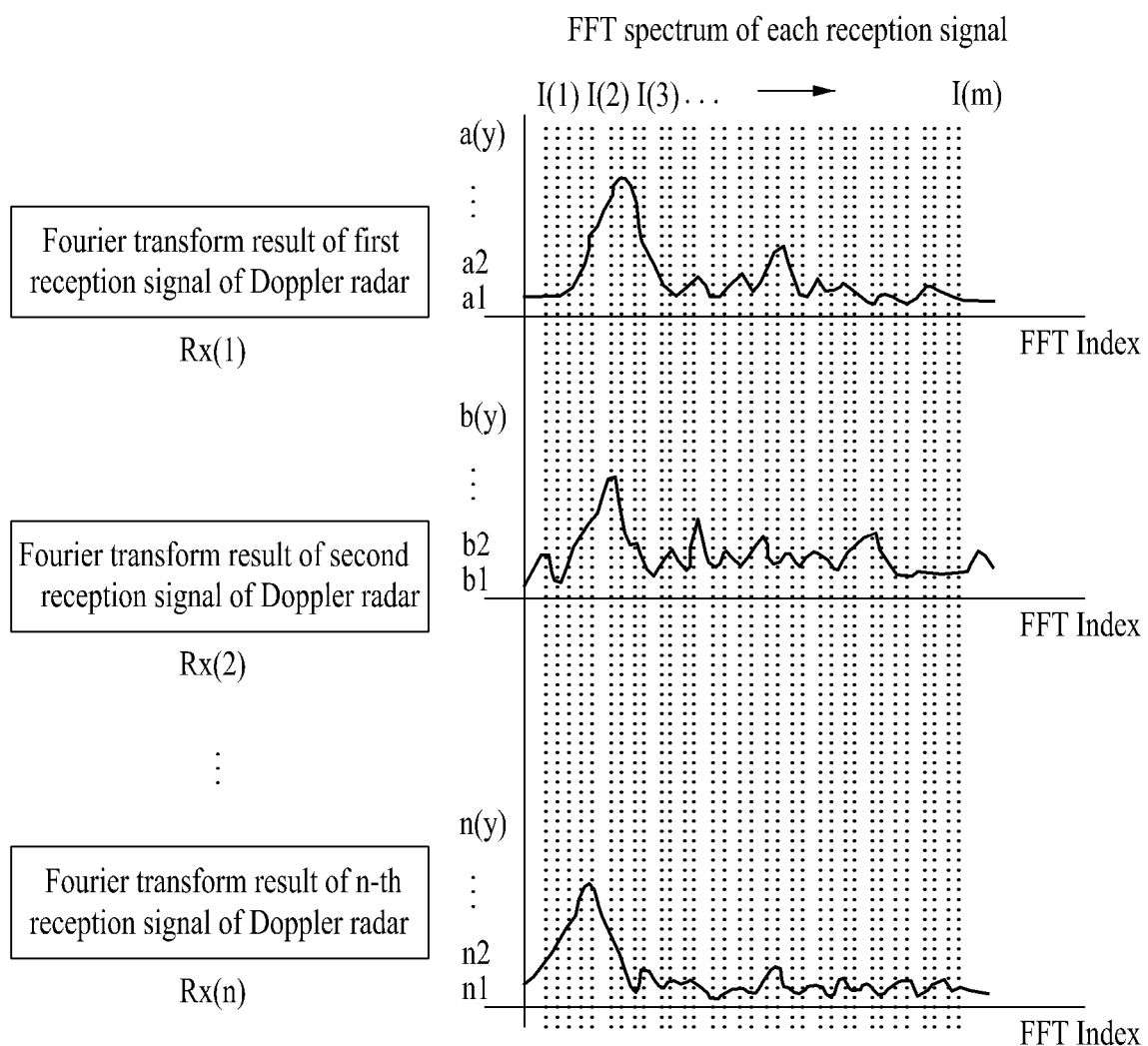
FIG. 7 is a graph showing a result spectrum of Fourier transform of each reception unit of a microwave Doppler radar in an apparatus for removing random noises of a radar collection signal in a biometric signal measurement radar according to the present invention.

Furthermore, in the spectrum graph of FIG. 7, although a commonly-generated periodic signal maintains a constant value, since an uncommon aperiodic signal is lowered to a remarkably small value, the spectrum deviation between the periodic signal and the aperiodic signal can be generated. That is, the frequency domain index set I(m) is calculated as I(1)=a1+b1+c1 ... (n)1, I(2)=a2+b2+c2 ... (n)2, I(3)=a3+b3+c3 ... (n)3, I(m)=a(m)+b(m)+c(m) ... (n) (m), and the like, and when the number of the reception antennas (Rx-1 to Rx-n) is n, the calculation result of each index is calculated as I(1)/n, I(2)/n, I(3)/n, ... I(m)/n.

In addition, the digital filtering signal processor 40 classifies deviation between spectrum components of a commonly-generated periodic signal and an uncommon aperiodic signal, for the value calculated by the calculation unit 32, according to a predetermined reference threshold value, and obtains only the periodic signal through filtering (S7). At this point, when the deviation is classified based on the threshold value, only a value larger than a reference point may be left, and this increases the possibility of being a biometric signal having a component periodic over time.

In this way, commonly received parts among the data received through each of the reception antennas Rx-1 to Rx-n may be taken, and uncommon parts are considered as random noises and removed by filtering.

As described above, compared to a conventional method of measuring biometric signals using a biometric signal measurement Doppler radar configured of a single transceiver, the present invention has an advantage of improving accuracy of sensing biometric signals in a contactless manner by effectively removing random noises included in a biometric signal area by the biometric signal measurement Doppler radar including a single transmission unit and multiple reception units.

Although the present invention has been shown and described in relation to specific embodiments in the above description, those skilled in the art may easily know that various modifications and changes are possible without departing from the spirit and scope of the present invention as defined by the claims.

The invention claimed is:

1. A method of removing random noises of a radar collection signal in a biometric signal measurement radar, the method comprising the steps of:
   (a) generating, by a voltage-controlled oscillator (VCO) of an IF signal generator, an oscillation frequency of a predetermined period using a voltage V(t) applied from the outside, transmitting the generated oscillation frequency to a major portion of a dynamic target through a single transmission antenna, and receiving, by n reception antennas, a signal reflected from the dynamic target and various types of signals generated around the dynamic target;
   (b) generating, by the IF signal generator, a Doppler IF signal from each of the n received signals;
   (c) converting, by an analog/digital converter, each of multiple Doppler IF signals input from the IF signal generator into digital data;
   (d) configuring digital signals collected by the analog/digital converter during a unit time into a data set having symbols at sampling time intervals by a Fast Fourier Transformer, and converting the data set into a frequency component symbol set having multiple indices;
   (e) calculating a value by adding, for each index set, index symbols converted into a frequency component symbol set and then dividing by the number of the n reception antennas by a calculation unit of a signal calculator; and
   (f) classifying deviation between spectrum components of a commonly-generated periodic signal and an uncommon aperiodic signal, for the value calculated by the calculation unit, according to a predetermined reference threshold value, and obtaining only the periodic signal through filtering.

2. An apparatus for removing random noises of a radar collection signal in a biometric signal measurement radar, the apparatus comprising:
   an IF signal generator for generating an oscillation frequency of a predetermined period using a voltage V(t) applied from the outside by a voltage-controlled oscillator and transmitting the oscillation frequency through a single transmission antenna Tx, receiving a reflection wave reflected from a radar signal collection area including a dynamic target at a predetermined distance through a plurality of reception antennas Rx-1 to Rx-n, and generating a Doppler IF signal from the received n signals;
   an analog/digital converter for converting the n analog signals generated by the IF signal generator into digital signals;
   a signal calculator for configuring the digital signals collected by the analog/digital converter during a unit time into a data set having symbols at sampling time intervals by a Fast Fourier Transformer, converting the configured data set into a frequency component symbol set of indices, and calculating a value by adding, for each index set, index symbols and then dividing by the number of the n reception antennas Rx by the calculation unit; and
   a digital filtering signal processor for filtering after classifying deviation between spectrum components of a commonly-generated periodic signal and an uncommon aperiodic signal, for the value calculated by the signal calculator, according to a predetermined reference threshold value.

3. The apparatus according to claim 2, wherein the reception antennas Rx-1 to Rx-n are arranged in a position and direction capable of simultaneously receiving signals from the dynamic target and other areas.

4. The apparatus according to claim 2, wherein in the digital filtering signal processor, any one among a band-pass filter (BPF), a high-pass filter (HPF), or a low-pass filter (LPF) of a predetermined band is applied in order to filter according to a reference threshold value.

* * * * *